United States Patent
Raymond et al.

(10) Patent No.: US 9,206,397 B2
(45) Date of Patent: Dec. 8, 2015

(54) HIGH EFFICIENCY FLP SITE-SPECIFIC RECOMBINATION IN MAMMALIAN CELLS USING AN OPTIMIZED FLP GENE

(75) Inventors: Christopher Raymond, Hoboken, NJ (US); Philippe Soriano, New York, NY (US)

(73) Assignee: The Fred Hutchinson Cancer Research Center, Seattle, WA (US)

( * ) Notice: Subject to any disclaimer, the term of this patent is extended or adjusted under 35 U.S.C. 154(b) by 1717 days.

(21) Appl. No.: 12/307,418

(22) PCT Filed: Jun. 21, 2007

(86) PCT No.: PCT/US2007/014482
§ 371 (c)(1),
(2), (4) Date: May 5, 2009

(87) PCT Pub. No.: WO2008/008160
PCT Pub. Date: Jan. 17, 2008

(65) Prior Publication Data
US 2010/0050279 A1    Feb. 25, 2010

Related U.S. Application Data (60) Provisional application No. 60/819,089, filed on Jul. 7, 2006.

(51) Int. Cl.
| | |
|---|---|
| A61K 48/00 | (2006.01) |
| C12N 15/63 | (2006.01) |
| C12N 15/09 | (2006.01) |
| C07H 21/04 | (2006.01) |
| C12N 9/00 | (2006.01) |
| C12N 15/79 | (2006.01) |

(52) U.S. Cl.
CPC *C12N 9/00* (2013.01); *C07H 21/04* (2013.01); *C12N 15/63* (2013.01); *C12N 15/79* (2013.01); *C12N 2510/00* (2013.01); *C12N 2800/30* (2013.01)

(58) Field of Classification Search
CPC .... C12N 15/63; C12N 15/79; C12N 2510/00; C07H 21/04
USPC ............ 424/93.21; 435/320.1, 455; 536/23.2
See application file for complete search history.

(56) References Cited

U.S. PATENT DOCUMENTS

| | | |
|---|---|---|
| 5,885,836 A | 3/1999 | Wahl et al. |
| 6,040,430 A | 3/2000 | Stewart |
| 6,175,058 B1 | 1/2001 | Baszczynski et al. |
| 6,461,864 B1 | 10/2002 | Soriano et al. |
| 6,534,314 B1 | 3/2003 | Bouhassira et al. |
| 6,541,231 B1 | 4/2003 | Baszczynski et al. |
| 6,720,475 B1 | 4/2004 | Baszczynski et al. |
| 6,774,279 B2 | 8/2004 | Dymecki |
| 2002/0166138 A1 | 11/2002 | Wahl et al. |
| 2003/0186291 A1 | 10/2003 | Faust et al. |
| 2004/0205838 A1 | 10/2004 | Dymecki |

OTHER PUBLICATIONS

Gustafsson et al. (2004) Codon bias and heterologous protein expression. Trends in Biotechnology 22(7): 346-353.*
Houdebine, L-M., 2002, Journal of Biotechnology, vol. 98, p. 145-160.*
Goldman et al., 2004, Med Sci Monit, vol. 10, No. 11, RA274-285.*
Sigmund, C., Jun. 2000, Arterioscler. Thromb. Vasc. Biol., p. 1425-1429.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Gorecki, D., 2001, Expert Opin. Emerging Drugs, 6(2): 187-198.*
Bennett, J., 2003, Gene Therapy, vol. 10, p. 977-982.*
Thomas et al., 2003, Nature Reviews/ Genetics, vol. 4, p. 346-358.*
Kodama et al., 2006, Current Medicinal Chemistry, vol. 13, p. 2155-2161.*
International Search Report and Written Opinion, PCT/US07/14482, mailed Sep. 30, 2008.
Buchholz F et al. Improved properties of FLP recombinase evolved by cycling mutagenesis. Nature Biotechnology, 1998, 16: 657-662.
Dymecki SM. FLP recombinase promotes site-specific DNA recombination in embryonic stem cells and transgenic mice. Proc. Natl. Acad. Sci. Usa, 1996, 93: 6191-6196.
Ikemura T. Codon usage and tRNA content in unicellular and multicellular organisms. Mol. Biol. Evol., 1985, 2(1): 13-34.
Schaft et al. Efficient FLP recombination in mouse ES cells and oocytes. Genesis, 2001, 31: 6-10.
Blast Report for FLPo, 2006, 20 pp.
Blast Report for PhiC3Io, 2006, 17 pp.

* cited by examiner

*Primary Examiner* — Shin Lin Chen
(74) *Attorney, Agent, or Firm* — Myers Bigel Sibley & Sajovec, P.A.

(57) ABSTRACT

The present invention provides an optimized FLP site-specific recombinase coding sequence and methods for its use. This genetically engineered FLP gene displays a marked increase in recombination efficiency compared to the native FLP gene and is therefore useful in a wide array of molecular applications.

32 Claims, 6 Drawing Sheets

```
    GGGCGAATTGGGTACCGATATCGCCGCCACCATGAGCCAGTTCGACATCCTGTGCAAGAC
1   ----------+---------+---------+---------+---------+---------+
    CCCGCTTAACCCATGGCTATAGCGGCGGTGGTACTCGGTCAAGCTGTAGGACACGTTCTG
                                  M  S  Q  F  D  I  L  C  K  T

CCCCCCCAAGGTGCTGGTGCGGCAGTTCGTGGAGAGATTCGAGAGGCCCAGCGGCGAGAA
61  ----------+---------+---------+---------+---------+---------+
    GGGGGGGTTCCACGACCACGCCGTCAAGCACCTCTCTAAGCTCTCCGGGTCGCCGCTCTT
     P  P  K  V  L  V  R  Q  F  V  E  R  F  E  R  P  S  G  E  K

GATCGCCAGCTGTGCCGCCGAGCTGACCTACCTGTGCTGGATGATCACCCACAACGGCAC
121 ----------+---------+---------+---------+---------+---------+
    CTAGCGGTCGACACGGCGGCTCGACTGGATGGACACGACCTACTAGTGGGTGTTGCCGTG
     I  A  S  C  A  A  E  L  T  Y  L  C  W  M  I  T  H  N  G  T

CGCCATCAAGAGGGCCACCTTCATGAGCTACAACACCATCATCAGCAACAGCCTGAGCTT
181 ----------+---------+---------+---------+---------+---------+
    GCGGTAGTTCTCCCGGTGGAAGTACTCGATGTTGTGGTAGTAGTCGTTGTCGGACTCGAA
     A  I  K  R  A  T  F  M  S  Y  N  T  I  I  S  N  S  L  S  F

CGACATCGTGAACAAGAGCCTGCAGTTCAAGTACAAGACCCAGAAGGCCACCATCCTGGA
241 ----------+---------+---------+---------+---------+---------+
    GCTGTAGCACTTGTTCTCGGACGTCAAGTTCATGTTCTGGGTCTTCCGGTGGTAGGACCT
     D  I  V  N  K  S  L  Q  F  K  Y  K  T  Q  K  A  T  I  L  E

GGCCAGCCTGAAGAAGCTGATCCCCGCCTGGGAGTTCACCATCATCCCTTACAACGGCCA
301 ----------+---------+---------+---------+---------+---------+
    CCGGTCGGACTTCTTCGACTAGGGGCGGACCCTCAAGTGGTAGTAGGGAATGTTGCCGGT
     A  S  L  K  K  L  I  P  A  W  E  F  T  I  I  P  Y  N  G  Q

GAAGCACCAGAGCGACATCACCGACATCGTGTCCAGCCTGCAGCTGCAGTTCGAGAGCAG
361 ----------+---------+---------+---------+---------+---------+
    CTTCGTGGTCTCGCTGTAGTGGCTGTAGCACAGGTCGGACGTCGACGTCAAGCTCTCGTC
     K  H  Q  S  D  I  T  D  I  V  S  S  L  Q  L  Q  F  E  S  S

CGAGGAGGCCGACAAGGGCAACAGCCACAGCAAGAAGATGCTGAAGGCCCTGCTGTCCGA
421 ----------+---------+---------+---------+---------+---------+
    GCTCCTCCGGCTGTTCCCGTTGTCGGTGTCGTTCTTCTACGACTTCCGGGACGACAGGCT
     E  E  A  D  K  G  N  S  H  S  K  K  M  L  K  A  L  L  S  E

GGGCGAGAGCATCTGGGAGATCACCGAGAAGATCCTGAACAGCTTCGAGTACACCAGCAG
481 ----------+---------+---------+---------+---------+---------+
    CCCGCTCTCGTAGACCCTCTAGTGGCTCTTCTAGGACTTGTCGAAGCTCATGTGGTCGTC
     G  E  S  I  W  E  I  T  E  K  I  L  N  S  F  E  Y  T  S  R
```

FIGURE 4

```
541  GTTCACCAAGACCAAGACCCTGTACCAGTTCCTGTTCCTGGCCACATTCATCAACTGCGG
     ----------+---------+---------+---------+---------+---------+
     CAAGTGGTTCTGGTTCTGGGACATGGTCAAGGACAAGGACCGGTGTAAGTAGTTGACGCC
      F  T  K  T  K  T  L  Y  Q  F  L  F  L  A  T  F  I  N  C  G

601  CAGGTTCAGCGACATCAAGAACGTGGACCCCAAGAGCTTCAAGCTGGTGCAGAACAAGTA
     ----------+---------+---------+---------+---------+---------+
     GTCCAAGTCGCTGTAGTTCTTGCACCTGGGGTTCTCGAAGTTCGACCACGTCTTGTTCAT
      R  F  S  D  I  K  N  V  D  P  K  S  F  K  L  V  Q  N  K  Y

661  CCTGGGCGTGATCATTCAGTGCCTGGTGACCGAGACCAAGACAAGCGTGTCCAGGCACAT
     ----------+---------+---------+---------+---------+---------+
     GGACCCGCACTAGTAAGTCACGGACCACTGGCTCTGGTTCTGTTCGCACAGGTCCGTGTA
      L  G  V  I  I  Q  C  L  V  T  E  T  K  T  S  V  S  R  H  I

721  CTACTTTTTCAGCGCCAGAGGCAGGATCGACCCCCTGGTGTACCTGGACGAGTTCCTGAG
     ----------+---------+---------+---------+---------+---------+
     GATGAAAAAGTCGCGGTCTCCGTCCTAGCTGGGGGACCACATGGACCTGCTCAAGGACTC
      Y  F  F  S  A  R  G  R  I  D  P  L  V  Y  L  D  E  F  L  R

781  GAACAGCGAGCCCGTGCTGAAGAGAGTGAACAGGACCGGCAACAGCAGCAGCAACAAGCA
     ----------+---------+---------+---------+---------+---------+
     CTTGTCGCTCGGGCACGACTTCTCTCACTTGTCCTGGCCGTTGTCGTCGTCGTTGTTCGT
      N  S  E  P  V  L  K  R  V  N  R  T  G  N  S  S  S  N  K  Q

841  GGAGTACCAGCTGCTGAAGGACAACCTGGTGCGCAGCTACAACAAGGCCCTGAAGAAGAA
     ----------+---------+---------+---------+---------+---------+
     CCTCATGGTCGACGACTTCCTGTTGGACCACGCGTCGATGTTGTTCCGGGACTTCTTCTT
      E  Y  Q  L  L  K  D  N  L  V  R  S  Y  N  K  A  L  K  K  N

901  CGCCCCCTACCCCATCTTCGCTATCAAGAACGGCCCTAAGAGCCACATCGGCAGGCACCT
     ----------+---------+---------+---------+---------+---------+
     GCGGGGGATGGGGTAGAAGCGATAGTTCTTGCCGGGATTCTCGGTGTAGCCGTCCGTGGA
      A  P  Y  P  I  F  A  I  K  N  G  P  K  S  H  I  G  R  H  L

961  GATGACCAGCTTTCTGAGCATGAAGGGCCTGACCGAGCTGACAAACGTGGTGGGCAACTG
     ----------+---------+---------+---------+---------+---------+
     CTACTGGTCGAAAGACTCGTACTTCCCGGACTGGCTCGACTGTTTGCACCACCCGTTGAC
      M  T  S  F  L  S  M  K  G  L  T  E  L  T  N  V  V  G  N  W

1021 GAGCGACAAGAGGGCCTCCGCCGTGGCCAGGACCACCTACACCCACCAGATCACCGCCAT
     ----------+---------+---------+---------+---------+---------+
     CTCGCTGTTCTCCCGGAGGCGGCACCGGTCCTGGTGGATGTGGGTGGTCTAGTGGCGGTA
      S  D  K  R  A  S  A  V  A  R  T  T  Y  T  H  Q  I  T  A  I
```

FIGURE 4 (Cont'd.)

```
        CCCCGACCACTACTTCGCCCTGGTGTCCAGGTACTACGCCTACGACCCCATCAGCAAGGA
1081    ---------+---------+---------+---------+---------+---------+
        GGGGCTGGTGATGAAGCGGGACCACAGGTCCATGATGCGGATGCTGGGGTAGTCGTTCCT
         P  D  H  Y  F  A  L  V  S  R  Y  Y  A  Y  D  P  I  S  K  E

GATGATCGCCCTGAAGGACGAGACCAACCCCATCGAGGAGTGGCAGCACATCGAGCAGCT
1141    ---------+---------+---------+---------+---------+---------+
        CTACTAGCGGGACTTCCTGCTCTGGTTGGGGTAGCTCCTCACCGTCGTGTAGCTCGTCGA
         M  I  A  L  K  D  E  T  N  P  I  E  E  W  Q  H  I  E  Q  L

GAAGGGCAGCGCCGAGGGCAGCATCAGATACCCCGCCTGGAACGGCATCATCAGCCAGGA
1201    ---------+---------+---------+---------+---------+---------+
        CTTCCCGTCGCGGCTCCCGTCGTAGTCTATGGGGCGGACCTTGCCGTAGTAGTCGGTCCT
         K  G  S  A  E  G  S  I  R  Y  P  A  W  N  G  I  I  S  Q  E

GGTGCTGGACTACCTGAGCAGCTACATCAACAGGCGGATCTGATGAGATATCGAGCTCCA
1261    ---------+---------+---------+---------+---------+---------+
        CCACGACCTGATGGACTCGTCGATGTAGTTGTCCGCCTAGACTACTCTATAGCTCGAGGT
         V  L  D  Y  L  S  S  Y  I  N  R  R  I  *  *

GCTTTTGTTCCC
1321    ---------+--
        CGAAAACAAGGG
```

FIGURE 4 (Cont'd.)

HIGH EFFICIENCY FLP SITE-SPECIFIC RECOMBINATION IN MAMMALIAN CELLS USING AN OPTIMIZED FLP GENE

RELATED APPLICATIONS

This application is a national phase application of PCT Application PCT/US2007/014482, filed Jun. 21, 2007, and published in English on Jan. 17, 2008, as International Publication No. WO 2008/008160, and which claims the benefit under 35 U.S.C. §119(e) of U.S. Provisional Patent Application Ser. No. 60/819,089, filed Jul. 7, 2006, the disclosure of each of which is incorporated herein by reference in its entirety.

GOVERNMENT SUPPORT

This invention was made with government support under HD024875 awarded by NIH. The government has certain rights in the invention.

FIELD OF THE INVENTION

The present invention provides compositions and methods directed to the use of an optimized FLP DNA site-specific recombinase coding sequence in mammalian cells.

BACKGROUND OF THE INVENTION

DNA site-specific recombinases (SSRs) are a powerful tool for analyzing gene function in eukaryotes. SSRs recognize specific DNA sequences (recognition sites) and catalyze recombination between two recognition sites. Upon binding to their recognition sites, SSRs can induce conditional gene inactivation or expression. If the two recognition sites are located on the same DNA molecule in the same orientation, the intervening DNA sequence is excised by the SSR from the parental molecule as a closed circle, leaving one recognition site on each of the reaction products. If the two sites are in inverted orientation, the recognition-site flanked region is inverted through recombinase-mediated recombination. Alternatively, if the two recognition sites are located on different molecules, recombinase-mediated recombination will lead to integration of a circular molecule or translocation between two linear molecules. These features make SSRs extremely useful for a number of applications in eukaryotic systems, including conditional activation of transgenes, chromosome engineering to obtain deletions, translocations or inversions, removal of selection marker genes, gene replacement, targeted insertion of transgenes, and the activation or inactivation of genes by inversion (see e.g., Branda, et al., *Dev. Cell.* 6 (1):7-28 (2004); Nagy, *Genesis.* 26 (2):99-109 (2000); Cohen-Tannoudji et al., *Mol. Hum. Reprod.* 4(10): 929-938 (1998)). The simultaneous use of multiple SSRs allows for the analysis of multiple gene knockouts or conditional gene expression.

The first widely used SSR in mammalian cultured cells and animals was the P1 bacteriophage-derived Cre gene (Sauer et al., *Proc. Natl. Acad. Sci. U.S.A.* 85 (14):5166-70 (1988); O'Gorman et al., *Science.* 251 (4999):1351-5 (1991); Lakso et al., *Proc. Natl. Acad Sci. U.S.A.* 89 (14):6232-6 (1992); Orban et al., *Proc. Natl. Acad. Sci. U.S.A.* 89 (15):6861-5 (1992)). Cre recognizes homotypic 34 base pair (bp) DNA sequences known as loxP sites and can induce the deletion, insertion, or inversion of DNA sequences depending on the number and orientation of loxP sites (Hoess et al., *Proc. Natl. Acad. Sci. U.S.A.* 9 (11):3398-402 (1982)). In addition to Cre, other SSRs have been shown to exhibit some activity in mammalian cells. These include the Kw recombinase of *Kluyveromyces waltii* (Ringrose et al., *Eur. J. Biochem.* 15:248 (3): 903-12 (1997)); mutant integrases of phage lamda (Lorbach et al., *J. Mol. Biol.* 296 (5):1175-81 (2000)); the integrases of phage HK022 (Kolot et al., *Mol. Biol. Rep.* 26 (3):207-13 (1999)); mutant gammadelta resolvase (Schwikardi et al., *FEBS. Lett.* 471 (2-3):147-50 (2000)); beta-recombinase (Diaz et al., *J. Biol. Chem.* 274 (10):6634-40 (1999)); and ΦC31 from *Streptomyces lividans* (Groth et al., *Proc. Natl. Acad. Sci. USA.* 97 (11):5995-6000 (2000); Belteki et al., *Nat. Biotechnol.* 21 (3):321-4 (2003)).

FLP from *Saccharomyces cerevisiae* is another SSR that has been used in mammals (Dymecki, *Proc. Natl. Acad. Sci. U.S.A.* 93 (12):6191-6 (1996)). Similar to Cre, FLP recognizes a distinct 34 bp sequence known as an FRT site, and can mediate the deletion, inversion, and insertion of DNA sequences between two of these sites (McLeod et al., *Mol. Cell Bio.* 6 (10):3357-67 (1986)). Initial use of FLP in mouse and mammalian cells revealed inefficient recombinase activity due to thermo-instability of the protein (Buchholz et al., *Nucleic Acids Res.* 24 (21):4256-62 (1996)). Subsequent screening for thermo-stable mutants resulted in the identification of an enhanced FLP recombinase (FLPe), which showed a 4-fold increase in recombination efficiency compared to endogenous FLP (Buchholz et al., Nat. Biotechnol. 16 (7):657-62 (1998)). Despite this improvement in thermo-stability, the recombination efficiency of FLP in mammalian cultured cells remains quite low. FLP has only been shown to exhibit at most a 6% recombination rate in mouse embryonic stem (ES) cell clones, with mosaic recombination found in almost all ES clones (Schaft et al., *Genesis.* 31 (1):6-10 (2001)). This low efficiency of recombination has hampered the use of FLP in cultured cells.

One reason for the low efficiency of these SSRs in mammalian cells may be their prokaryotic origin. For use in eukaryotic systems, SSRs should ideally be expressed at high levels. Often, achieving high steady-state expression levels of prokaryotic genes in mammalian systems can be difficult. One potential problem is that the amino acid codon usage differs greatly between prokaryotes and vertebrates (Ikemura, *Mol. Biol. Evol.* 2 (1):13-34 (1985)). Prokaryotic genes often contain a proportionally high-abundance of codons for tRNAs that are rare in vertebrates, resulting in low levels of expression (Grantham et al., *Nucleic Acids Res.* 9 (1):r43-r74 (1981)). A second potential problem associated with expression of prokaryotic genes in vertebrates is the presence of cryptic splice acceptor/donor sites, since prokaryotic genes do not normally undergo splicing in the native host. Another potential problem is that a high number of the DNA dinucleotide motif CpG may also result in gene silencing, since DNA methylation occurs at such cytosines in vertebrates. Additionally, the overall base composition of the prokaryotic gene can affect mRNA stability in eukaryotic cells. Prokaryotic genes with high A/T content often result in less stable mRNAs and thus low levels of expression.

Optimization of the endogenous gene can be used to improve expression, however, codon-optimization has to be performed individually for each new gene, taking into account all factors that can influence gene expression. Codon-optimized Cre genes with improved expression in mammals have been described previously (e.g., Koresawa et al., *Transplant Proc.* 32 (7):2516-17 (2000); PCT International Publication No. WO/2002/04609). A codon-optimized ΦC31 recombinase has also been reported. (U.S. Patent Publication No. 20030186291).

The present invention overcomes previous shortcomings in the art by providing a codon-optimized FLP (FLPo) SSR and methods for its use. This genetically engineered FLP gene displays a marked increase in recombination efficiency compared to the native FLP gene and is therefore useful in a wide array of molecular applications.

SUMMARY OF THE INVENTION

The present invention provides an optimized FLP gene having an enhanced recombinase activity. The present invention also includes constructs, cells, and transgenic organisms containing this gene and useful for a variety of genetic analysis and molecular biology applications.

Further provided by the present invention is a method of removing a selection cassette flanked by FLP recognition sequences using a novel, optimized FLP gene having an enhanced recombinase activity. The present invention also includes the cells and transgenic organisms produced using this method and useful for a variety of genetic analysis and molecular biology applications.

In further embodiments, the present invention provides a method for using multiple recombinases in a cell using a novel, optimized FLP gene having an enhanced recombinase activity. The present invention also includes the cells and transgenic organisms produced using this method and useful for a variety of genetic analysis and molecular biology applications.

DETAILED DESCRIPTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

DEFINITIONS

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

As used herein, the term "nucleic acid molecule" refers to a DNA or RNA molecule, including cDNA, a DNA fragment, genomic DNA, synthetic (e.g., chemically synthesized) DNA, plasmid DNA, mRNA, and anti-sense RNA. A nucleic acid may or may not be immediately contiguous with nucleotide sequences with which it is immediately contiguous (one on the 5' end and one on the 3' end) in the naturally occurring genome of the organism from which it is derived. The term includes, for example, a DNA molecule that is incorporated into a construct, into a vector, into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid nucleic acid.

As used herein, the term "nucleic acid sequence" or "sequence" refers to the sequence of nucleotides from the 5' to 3' end of nucleic acid molecule. Nucleic acid sequences provided herein are represented using the standard code for representing the nucleotide characters as set forth in the U.S. sequence rules, 37 CFR §§1.821-1.825 and the World Intellectual Property Organization (WIPO) Standard ST.25.

As used herein, the term "gene" refers to a nucleic acid molecule capable of being used to produce mRNA or anti-sense RNA. Genes may or may not be capable of being used to produce a functional protein.

As used herein, the term "coding sequence" refers to a nucleic acid molecule that codes for a protein sequence. A coding sequence can be used to produce a protein product. The coding sequence may or may not include non-coding regions such as introns, poly adenylation signals, and other untranslated regions. The coding sequence may or may not be fused to another coding sequence or localization signal, such as a nuclear localization signal. The coding sequence may be cloned into a vector or expression construct, may be integrated into a genome, or may be present as a DNA fragment.

As used herein, the term "optimized coding sequence" refers to a coding sequence that has been improved over the native coding sequence. Means of improvement include, but are not limited to, incorporating codon usage preferences, reducing rare codon usage, reducing CpG content, removing cryptic splice acceptor/donor sequences, changing overall nucleotide base composition, and engineering a Kozak translational initiation consensus sequence. An optimized coding sequence may or may not be produced synthetically (e.g., chemically synthesized).

As used herein, the term "enhanced recombinase activity" refers to the recombinase activity of gene product shoving increased activity when compared to the gene product of the native or endogenous gene. The recombinase activity can be measured in vivo or in vitro. Methods for measuring recombinase activity are provided herein, but are not limited to these methods alone.

As used herein, the term "construct" refers to a recombinant nucleic acid molecule comprising containing a cis-acting regulatory element such as a gene. A construct may be cloned into a vector such as an autonomously replicating plasmid or virus. The vector may be used to manipulate DNA molecules or to produce a transgenic organism or host cell. Such constructs and vectors, cells, and organisms containing such constructs are an aspect of the invention.

As used herein, the term "transforming" refers to causing a cell or organism to undergo genetic transformation. Genetic transformation is the genetic modification of a cell or organism by the uptake and incorporation of exogenous DNA. Genetic transformation used in practicing the methods of the present invention may be by any method known to one skilled in the art.

As used herein, the term "transgenic organism" refers to an organism having chromosomes into which one or more heterologous genes have been incorporated either artificially or naturally. Transgenic organisms of the present invention may be produced via the transformation of a cell or organism by any method known to one skilled in the art. Transgenic organisms of the present invention include all species of eukaryotic organisms.

As used herein, the term "selection cassette" refers to a construct useful for identifying or selecting desirable cells or organisms. Selection cassettes contain a selectable marker gene that results in positive or negative selection of cells or organisms harboring this gene. Selectable marker genes are well known to those skilled in the art and include, but are not limited to, antibiotic resistance genes. Selectable marker genes usually code for a gene product that the host cell cannot make naturally, such as specific antibiotic resistance factor. A selectable marker is used to ensure that the cell or organism has been transformed.

As used herein, the term "SSR" or "recombinase" refers to a DNA site-specific recombinase. SSRs recognize specific DNA sequences (recognition sites) and catalyze recombination between two recognition sites. SSRs for use in the present invention include, but are not limited to, the P1 bacteriophage-derived Cre gene (Sauer et al., *Proc. Natl. Acad. Sci. U.S.A.* 85 (14):5166-70 (1988); O'Gorman et al., *Science*. 251 (4999):1351-5 (1991); Lakso et al., *Proc. Natl. Acad. Sci. U.S.A.* 89 (14):6232-6 (1992); Orban et al., *Proc. Natl. Acad Sci. USA.* 89 (15):6861-5 (1992)); Kw recombinase of *Kluyveromyces waltii* (Ringrose et al., *Eur. J Biochem.* 15:248 (3):903-12 (1997)); mutant integrases of phage lamda (Lorbach et al., *J. Mol. Biol.* 296 (5):1175-81 (2000)); the integrases of phage HK022 (Kolot et al., *Mol. Biol. Rep.* 26 (3):207-13 (1999)); mutant gammadelta resolvase (Schwikardi et al., *FEBS Lett.* 471 (2-3):147-50 (2000)); beta-recombinase (Diaz et al., *J. Biol. Chem.* 274 (10):6634-40 (1999)); ΦC31 from *Streptomyces lividans* (Groth et al., *Proc. Natl. Acad. Sci. U.S.A.* 97 (11):5995-6000 (2000); Belteki et al., *Nat. Biotechnol.* 21 (3):321-4 (2003)); and other mutations and optimized versions of SSR genes (e.g., PCT International Publication No. WO/2002104609; U.S. Patent Publication No. 20030186291).

As used herein, the term "recognition site" refers to a specific DNA sequence that is recognized by a SSR. The SSR binds the recognition site and catalyzes recombination between two recognition sites. Each SSR has specific recognition sites. For example, FLP recognizes a distinct 34 bp sequence known as an FLP recombinase target (FRT) site, and can mediate the deletion, inversion, and insertion of DNA sequences between two of these sites (McLeod et al., *Mol. Cell Bio.* 6 (10):3357-67 (1986)).

As used herein, the term "sequence identity" refers to the percentage of identical nucleotides between two sequences in a sequence alignment. Sequence identity is calculated by producing a sequence alignment optimally aligning a first nucleic acid sequence to a reference nucleic acid sequence with appropriate nucleotide insertions or deletions over the window of comparison. A sequence alignment is an arrangement of two or more sequences highlighting their similarity. Gaps may be introduced in the sequences so that wherever possible the nucleotides at each position in the alignment are identical. Compositions of this invention include an optimized FLP recombinase coding sequence having at least about 70% identity, more preferably about 80% identity, and most preferably about 90% identity over a comparison window of at least about 1000 nucleotide positions, more preferably at least about 1150 nucleotide positions, and most preferably over the entire length of the nucleic acid sequence provided as SEQ ID NO:1. Pair-wise sequence alignment methods producing optimal sequence alignments are well known to those skilled in the art. Ideal methods include computerized implementations of the Needleman-Wunsch algorithm or the Smith Waterman algorithms (available as the GCG Wisconsin® Package or Accelrys GCG® from Accelrys Software Inc., San Diego Calif.). The optimized FLP recombinase coding sequence may be a full-length molecule or a portion of a longer molecule.

Thus in one embodiment, this invention provides an optimized FLP coding sequence having an enhanced recombinase activity in a cell containing and expressing the optimized FLP gene. Our results demonstrate significantly enhanced recombinase activity with the optimized FLPo gene as compared to the native FLP gene, FLPe. This enhanced recombination efficiency facilitates the use of the FLP recombinase in a wider array of molecular applications than was previously possible with the FLPe gene. These molecular applications include, but are not limited to, study of gene function, removal of selection cassettes used in gene targeting, tissue-specific gene knockouts, and controlling or modulating gene expression in specific cell types or tissues.

The present invention also includes constructs, cells, and transgenic organisms produced using an optimized FLP coding sequence and useful for a variety of genetic analysis and molecular biology applications. The cells and transgenic organisms of the present invention may or may not contain the optimized FLP coding sequence.

In another embodiment, this invention provides a method for the efficient removal of a selection cassette flanked by FLP recombinase recognition sites (FRT sites) using the optimized FLP gene provided herein. The increase in recombination efficiency with the optimized FLPo coding sequence facilitates the use of the FLP recombinase in cultured cells and transgenic organisms such as transgenic mice. To date, the use of FLP in cultured cells has been hampered by the low efficiency of recombination. In one embodiment, this method can be used in cultured cells for removing a positive selection cassette flanked by FLP recombinase recognition sites. Such selection cassettes may be used in gene targeting in cultured ES cells. Often the removal of such a selection cassette, which is required to generate a "clean" targeted allele, is not performed in culture due to the inefficient and incomplete FLP-mediated recombination in ES cells. Removal of a FRT-mediated cassette can be done in vivo by crossing mice to a general "FLP-deletor" mouse stain (Farley et al., *Genesis*. 28 (3-4):106-10 (2000)). However, the drawback to this approach is the extra time required for breeding of mice. The present invention solves this problem by providing a method for efficient and complete FLP-mediated recombination in ES cells, thus facilitating the removal of the selection cassette in cell culture. The present invention also includes cells and transgenic organisms produced using this method.

In another embodiment, this invention provides a method for using multiple, highly efficient SSRs in cells and transgenic organisms using the optimized FLP gene provided herein. Other recombinases for use in this invention include any SSR that recognizes specific recognition sites in a cell or transgenic organism and can catalyze recombination between the two recognition sites. This method can be used for broad range of molecular manipulations, including, but not limited to performing multiple general or tissue-specific gene knockouts, studying gene function at the intersection of overlapping expression, and controlling gene expression in a temporal "off-on-off" manner in single or multiple cell types or tissues. The present invention also includes cells and transgenic organisms produced using this method.

The methods and compositions of the present invention are useful in eukaryotic systems for a number of applications including, but not limited to, conditional activation and/or inactivation of transgenes and/or endogenouos genes; chromosome engineering to obtain deletions, translocations, insertions, or inversions; removal of selection marker genes; gene replacement; targeted insertion of transgenes; and the activation and/or inactivation of genes by inversion. Eukaryotic systems or organisms useful in practicing the present invention include, but are not limited to, vertebrates such as fish, amphibians, reptiles, birds, and mammals as well as invertebrates such as sponges, jellyfish, planarians, worms, starfish, sea urchins, sea cucumbers, mollusks, and arthropods.

EXAMPLES

Site-Specific Recombinase Genes and Expression Vectors

Figure 1:
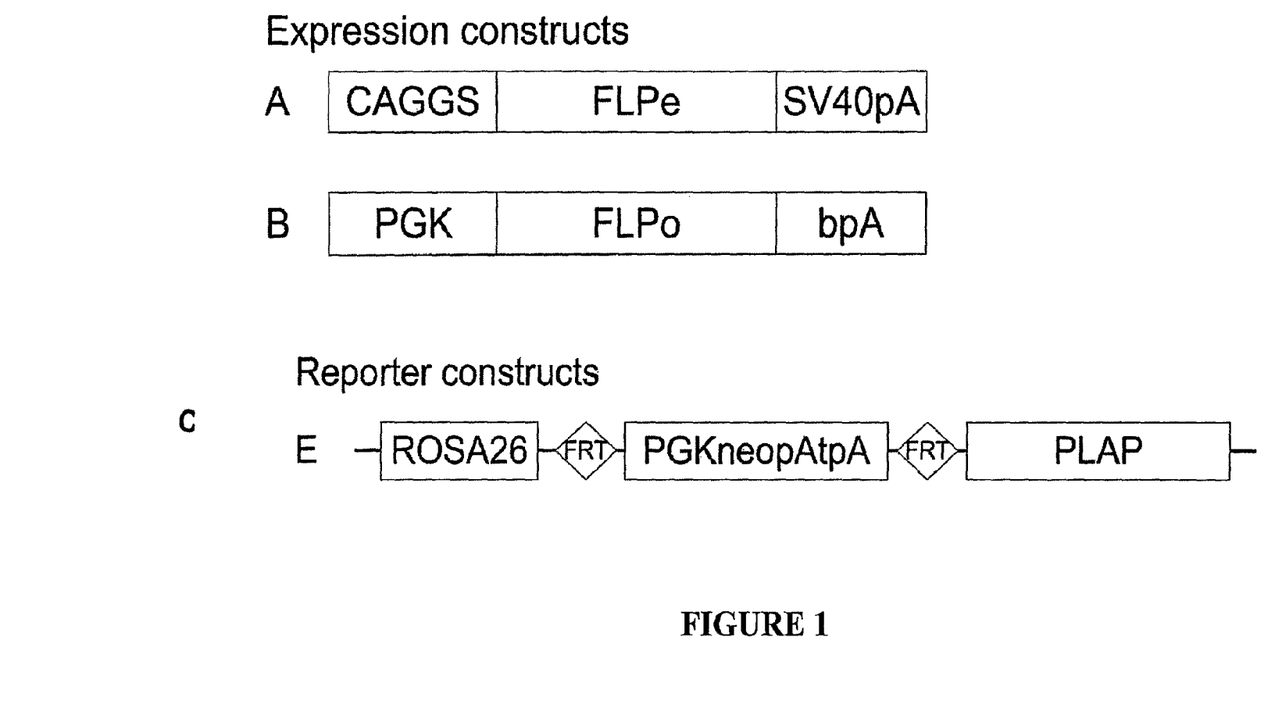
FIG. 1 depicts expression and reporter constructs of the present invention. The following abbreviations are used: CAGGS, FLPe (FLPe coding sequence), SV40pA (SV40 polyadenylation signal), PGK (phosphor-glycerate kinase promoter), bpA (bovine growth hormone polyadenylation signal), ROSA26 (ROSA26 locus), FRT (FLP recognition site), PGKneopATpA, PLAP (PLAP reporter gene).

An optimized FLP coding sequence (FLPo) (provided as SEQ ID NO:1) was commercially synthesized de novo (Geneart GmbH, Regensburg, Germany) according to the FLPe amino acid sequence (Buchholz et al., *Nat. Biotechnol.* 16 (7):657-62 (1998)). FLPo was designed with mouse codon usage in order to increase translational efficiency in mammalian cells. FLPo also has an increased G|C nucleotide content to prolong mRNA half-life. FLPo was also engineered to include a Kozak consensus translational start sequence, two transcriptional stop sequences, and a bovine growth hormone polyadenylation sequence to increase the efficiency of transcription and translation in vertebrate cells. The FLPo coding sequence was blunt cloned into a mammalian expression vector driven by the high expressing phospho-glycerate kinase (PGK) promoter to generate the expression vector PGKFLPo (FIG. 1B). The CAGGSFLPe expression construct, containing the FLPe coding sequence for transient expression of FLPe in mouse ES cells, was a gift from A. F. Stewart (FIG. 1A). CAGGSFLPe was previously reported to give the highest efficiency of FLP-mediated recombination in ES cells (Schaft et al., *Genesis.* 31 (1).6-10 (2001)).

Analysis of FLP Recombinase Efficiency in ES Cells

Figure 2:
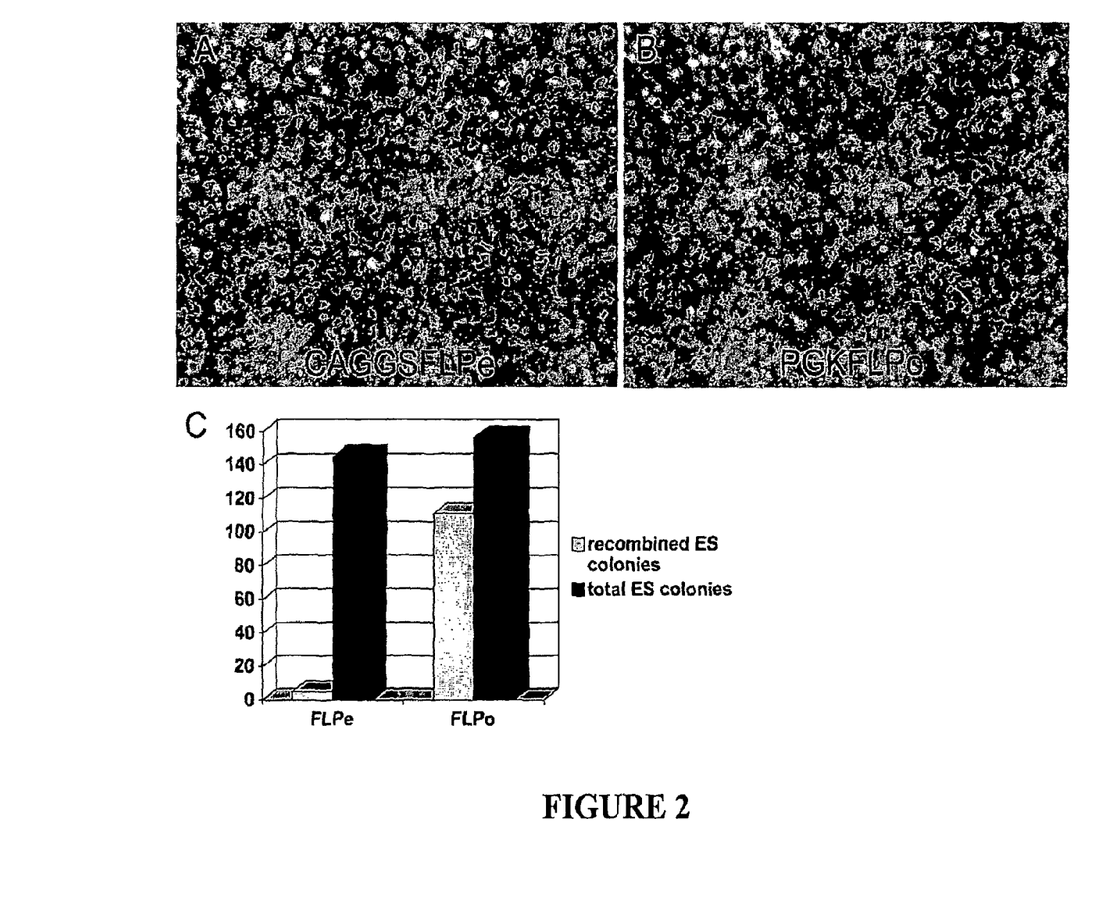
FIG. 2 shows the results of an alkaline phosphatase reporter analysis of FLP-mediated recombination activity in FLP reporter ES cells.

The recombination efficiency of codon-optimized FLPo was compared to FLPe using FLP reporter ES cells. FLP reporter ES cells harbor a FLP-inducible PLAP reporter gene integrated at the broadly expressed ROSA26 locus (FIG. 1C). These cells were used as previously described to monitor FLP recombination activity (Awatramani et al., *Nat. Genet.* 29 (3):257-9 (2001)). FLP reporter ES cells were electroporated with 10 μg of circular CAGGSFLPe or PGKFLPo. Alkaline phosphatase reporter activity was measured after 5 days in culture (FIGS. 2A and 2B). A majority of the ES colonies displayed some degree of FLP-mediated recombination activity when transfected with PGKFLPo (FIG. 2B). In contrast, very little FLP-mediated recombination activity was observed in ES cells transfected with the CAGGSFLPe vector (FIG. 2A). Quantitation of alkaline phosphatase reporter activity revealed that nearly 75% of ES cell colonies transfected with FLPo displayed either mosaic or complete recombination (FIG. 2C). This represents nearly a 20-fold increase in recombination activity for codon-optimized FLPo over FLPe.

Figure 3:
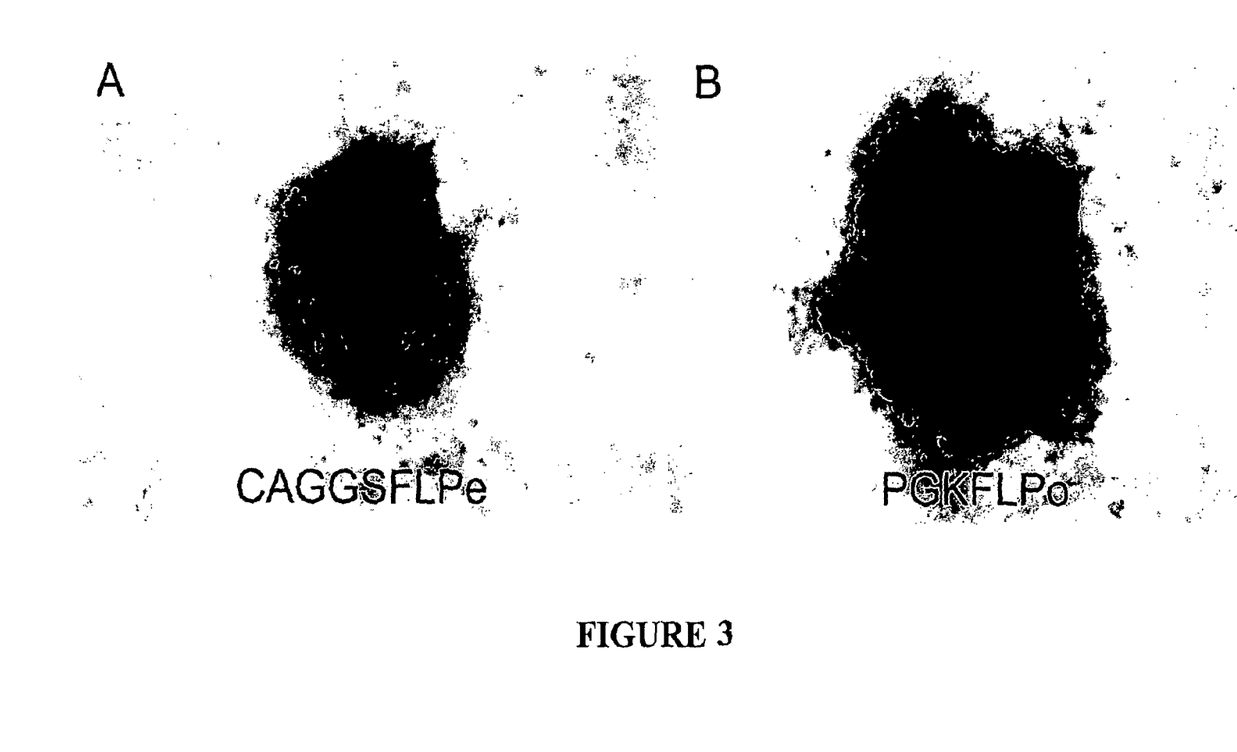
FIG. 3 depicts shows the results of an alkaline phosphatase reporter analysis of FLP-mediated recombination activity in cultured FLP reporter ES cells.
Figure 4:
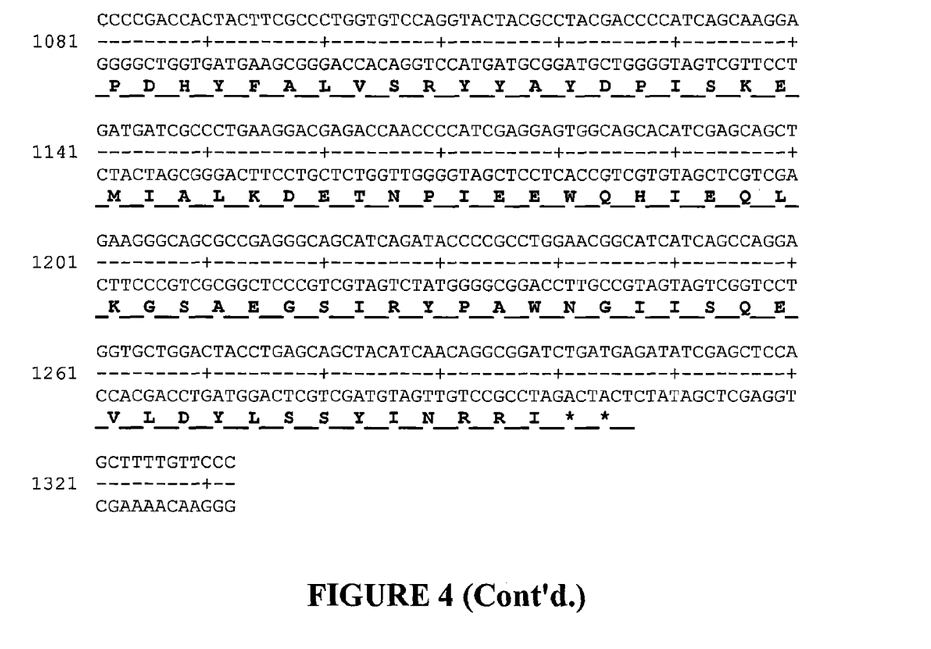
FIG. 4 illustrates the nucleic acid sequence of the FLPo gene provided as SEQ ID NO:1 with the amino acid translation provided beneath the nucleic acid sequence.

The ability of codon-optimized FLPo to mediate full recombination in an ES cell colony was tested in FLP reporter ES cells. Cells were co-electroporated with linearized PGK-FLPo or CAGGSFLPe DNA in a 10:1 molar ratio with linearized PGKHygromycin. ES cells were then treated with hygromycin for 10 days, and the hygromycin-resistant (hygro$^R$) ES colonies were stained for alkaline phosphatase activity. The staining indicated that ES cells harboring an integrated codon-optimized FLPo expression vector underwent complete recombination in cultured cells (FIG. 3B). In comparison, ES cell colonies containing an integrated FLPe construct showed only background alkaline phosphatase staining (FIG. 3A). Quantitation of these results showed that 0/10 ES cell colonies with an integrated CAGGSFLPe expression vector showed recombination activity, while 7/14 ES cell colonies harboring an integrated codon-optimized FLPo vector showed recombination activity (Table 1). This demonstrates that the genetically engineered FLPo gene displays a marked increase in recombination efficiency in ES cells compared to the native FLP gene.

TABLE 1

Recombination Efficiency in ES Cell Colonies

| Construct | Number of Hyro$^R$ colonies | Number of recombined colonies |
|---|---|---|
| CAGGSFLPe | 10 | 0 |
| PGKFLPo | 14 | 7 |

Except as otherwise indicated, standard methods known to those skilled in the art may be used for the construction and use of nucleic acid molecules, vectors, selectable markers, cells, transgenic organisms, and the like. Such techniques are well known to those skilled in the art. See, e.g., J. Sambrook et al., *Molecular Cloning: A Laboratory Manual* 3rd Ed. (2001) (Cold Spring Harbor Laboratory Press; Woodbury, N.Y.); *Current Protocols In Molecular Biology*, edited by F. M. Ausubel et al. (John Wiley & Sons, Inc.; Hoboken, N.J.); and *Current Protocols in Cell Biology*, edited by Juan S. Bonifacino, et al. (John Wiley & Sons, Inc.; Hoboken, N.J.).

All publications patents, and patent publications cited herein are incorporated by reference in their entireties for the teachings relevant to the sentence and/or paragraph in which the reference is presented.

We claim:

1. A nucleic acid molecule comprising an optimized FLP recombinase coding sequence having the sequence of SEQ ID NO:1 that provides enhanced recombinase activity in a cell comprising and expressing the nucleic acid molecule.

2. An expression construct comprising the nucleic acid molecule comprising the optimized FLP recombinase coding sequence of claim 1.

3. A method of preparing isolated cells comprising an optimized FLP recombinase coding sequence having the sequence of SEQ ID NO:1 that provides enhanced recombinase activity in a cell comprising and expressing the nucleic acid molecule, the method comprising transforming an isolated cell with the expression construct of claim 2.

4. The method of claim 3, wherein the isolated cells are eukaryotic cells.

5. The method of claim 4, wherein the isolated cells are invertebrate cells.

6. The method of claim 4, wherein the isolated cells are vertebrate cells.

7. The method of claim 6, wherein the isolated cells are mammalian cells.

8. The method of claim 7, wherein the isolated cells are mouse cells.

9. The method of claim 8, wherein the isolated mouse cells are mouse ES cells.

10. An isolated cell comprising the nucleic acid molecule comprising the optimized FLP recombinase coding sequence of claim 1.

11. The isolated cell of claim 10, wherein the isolated cell is a eukaryotic cell.

12. The isolated cell of claim 11, wherein the isolated cell is an invertebrate cell.

13. The isolated cell of claim 11, wherein the isolated cell is a vertebrate cell.

14. The isolated cell of claim 13, wherein the isolated cell is a mammalian cell.

15. The isolated cell of claim 14, wherein the isolated cell is a mouse cell.

16. The isolated mouse cell of claim 15, wherein the mouse cell is a mouse embryonic stem (ES) cell.

17. A nucleic acid molecule comprising an optimized FLP recombinase coding sequence having at least about 90% sequence identity to the sequence of SEQ ID NO:1 that provides enhanced recombinase activity in a cell comprising and expressing the nucleic acid molecule.

18. An expression construct comprising the nucleic acid molecule comprising the optimized FLP recombinase coding sequence of claim 17.

19. A method of preparing isolated cells comprising an optimized FLP recombinase coding sequence having at least about 90% sequence identity to the sequence of SEQ ID NO:1 that provides enhanced recombinase activity in a cell comprising and expressing the nucleic acid molecule, the method comprising transforming an isolated cell with the expression construct of claim 18.

20. The method of claim 19, wherein the isolated cells are eukaryotic cells.

21. The method of claim 20, wherein the isolated cells are invertebrate cells.

22. The method of claim 20, wherein the isolated cells are vertebrate cells.

23. The method of claim 22, wherein the isolated cells are mammalian cells.

24. The method of claim 23, wherein the isolated cells are mouse cells.

25. The method of claim 24, wherein the isolated mouse cells are mouse ES cells.

26. An isolated cell comprising the nucleic acid molecule comprising the optimized FLP recombinase coding sequence of claim 17.

27. The isolated cell of claim 26, wherein the isolated cell is a eukaryotic cell.

28. The isolated cell of claim 27, wherein the isolated cell is an invertebrate cell.

29. The isolated cell of claim 27, wherein the isolated cell is a vertebrate cell.

30. The isolated cell of claim 29, wherein the isolated cell is a mammalian cell.

31. The isolated cell of claim 30, wherein the isolated cell is a mouse cell.

32. The isolated cell of claim 31, wherein the mouse cell is a mouse ES cell.

* * * * *

SEQUENCE LISTING

<160> NUMBER OF SEQ ID NOS: 2

<210> SEQ ID NO 1
<211> LENGTH: 1332
<212> TYPE: DNA
<213> ORGANISM: Artificial

```
<220> FEATURE:
<223> OTHER INFORMATION: Optimized FLP (FLPo) coding sequence
<220> FEATURE:
<221> NAME/KEY: CDS
<222> LOCATION: (32)..(1300)
<223> OTHER INFORMATION: FLPo ORF

<400> SEQUENCE: 1
```

| | | | | | | | | | | | | | | | | |
|---|---|---|---|---|---|---|---|---|---|---|---|---|---|---|---|---|
| gggcgaattg | ggtaccgata | tcgccgccac | c | atg | agc | cag | ttc | gac | atc | ctg | | | | | | 52 |
| | | | | Met | Ser | Gln | Phe | Asp | Ile | Leu | | | | | | |
| | | | | 1 | | | | 5 | | | | | | | | |

| tgc | aag | acc | ccc | ccc | aag | gtg | ctg | gtg | cgg | cag | ttc | gtg | gag | aga | ttc | 100 |
|---|---|---|---|---|---|---|---|---|---|---|---|---|---|---|---|---|
| Cys | Lys | Thr | Pro | Pro | Lys | Val | Leu | Val | Arg | Gln | Phe | Val | Glu | Arg | Phe | |
| | | 10 | | | | 15 | | | | 20 | | | | | | |

| gag | agg | ccc | agc | ggc | gag | aag | atc | gcc | agc | tgt | gcc | gcc | gag | ctg | acc | 148 |
|---|---|---|---|---|---|---|---|---|---|---|---|---|---|---|---|---|
| Glu | Arg | Pro | Ser | Gly | Glu | Lys | Ile | Ala | Ser | Cys | Ala | Ala | Glu | Leu | Thr | |
| 25 | | | | | 30 | | | | | 35 | | | | | | |

| tac | ctg | tgc | tgg | atg | atc | acc | cac | aac | ggc | acc | gcc | atc | aag | agg | gcc | 196 |
|---|---|---|---|---|---|---|---|---|---|---|---|---|---|---|---|---|
| Tyr | Leu | Cys | Trp | Met | Ile | Thr | His | Asn | Gly | Thr | Ala | Ile | Lys | Arg | Ala | |
| 40 | | | | 45 | | | | | 50 | | | | | 55 | | |

| acc | ttc | atg | agc | tac | aac | acc | atc | atc | agc | aac | agc | ctg | agc | ttc | gac | 244 |
|---|---|---|---|---|---|---|---|---|---|---|---|---|---|---|---|---|
| Thr | Phe | Met | Ser | Tyr | Asn | Thr | Ile | Ile | Ser | Asn | Ser | Leu | Ser | Phe | Asp | |
| | | | | 60 | | | | | 65 | | | | | 70 | | |

| atc | gtg | aac | aag | agc | ctg | cag | ttc | aag | tac | aag | acc | cag | aag | gcc | acc | 292 |
|---|---|---|---|---|---|---|---|---|---|---|---|---|---|---|---|---|
| Ile | Val | Asn | Lys | Ser | Leu | Gln | Phe | Lys | Tyr | Lys | Thr | Gln | Lys | Ala | Thr | |
| | | 75 | | | | | 80 | | | | | 85 | | | | |

| atc | ctg | gag | gcc | agc | ctg | aag | aag | ctg | atc | ccc | gcc | tgg | gag | ttc | acc | 340 |
|---|---|---|---|---|---|---|---|---|---|---|---|---|---|---|---|---|
| Ile | Leu | Glu | Ala | Ser | Leu | Lys | Lys | Leu | Ile | Pro | Ala | Trp | Glu | Phe | Thr | |
| | | | 90 | | | | | 95 | | | | | 100 | | | |

| atc | atc | cct | tac | aac | ggc | cag | aag | cac | cag | agc | gac | atc | acc | gac | atc | 388 |
|---|---|---|---|---|---|---|---|---|---|---|---|---|---|---|---|---|
| Ile | Ile | Pro | Tyr | Asn | Gly | Gln | Lys | His | Gln | Ser | Asp | Ile | Thr | Asp | Ile | |
| 105 | | | | | 110 | | | | | 115 | | | | | | |

| gtg | tcc | agc | ctg | cag | ctg | cag | ttc | gag | agc | agc | gag | gag | gcc | gac | aag | 436 |
|---|---|---|---|---|---|---|---|---|---|---|---|---|---|---|---|---|
| Val | Ser | Ser | Leu | Gln | Leu | Gln | Phe | Glu | Ser | Ser | Glu | Glu | Ala | Asp | Lys | |
| 120 | | | | 125 | | | | | 130 | | | | | 135 | | |

| ggc | aac | agc | cac | agc | aag | aag | atg | ctg | aag | gcc | ctg | ctg | tcc | gag | ggc | 484 |
|---|---|---|---|---|---|---|---|---|---|---|---|---|---|---|---|---|
| Gly | Asn | Ser | His | Ser | Lys | Lys | Met | Leu | Lys | Ala | Leu | Leu | Ser | Glu | Gly | |
| | | | | 140 | | | | | 145 | | | | | 150 | | |

| gag | agc | atc | tgg | gag | atc | acc | gag | aag | atc | ctg | aac | agc | ttc | gag | tac | 532 |
|---|---|---|---|---|---|---|---|---|---|---|---|---|---|---|---|---|
| Glu | Ser | Ile | Trp | Glu | Ile | Thr | Glu | Lys | Ile | Leu | Asn | Ser | Phe | Glu | Tyr | |
| | | | 155 | | | | | 160 | | | | | 165 | | | |

| acc | agc | agg | ttc | acc | aag | acc | aag | acc | ctg | tac | cag | ttc | ctg | ttc | ctg | 580 |
|---|---|---|---|---|---|---|---|---|---|---|---|---|---|---|---|---|
| Thr | Ser | Arg | Phe | Thr | Lys | Thr | Lys | Thr | Leu | Tyr | Gln | Phe | Leu | Phe | Leu | |
| | | 170 | | | | | 175 | | | | | 180 | | | | |

| gcc | aca | ttc | atc | aac | tgc | ggc | agg | ttc | agc | gac | atc | aag | aac | gtg | gac | 628 |
|---|---|---|---|---|---|---|---|---|---|---|---|---|---|---|---|---|
| Ala | Thr | Phe | Ile | Asn | Cys | Gly | Arg | Phe | Ser | Asp | Ile | Lys | Asn | Val | Asp | |
| | | 185 | | | | | 190 | | | | | 195 | | | | |

| ccc | aag | agc | ttc | aag | ctg | gtg | cag | aac | aag | tac | ctg | ggc | gtg | atc | att | 676 |
|---|---|---|---|---|---|---|---|---|---|---|---|---|---|---|---|---|
| Pro | Lys | Ser | Phe | Lys | Leu | Val | Gln | Asn | Lys | Tyr | Leu | Gly | Val | Ile | Ile | |
| 200 | | | | 205 | | | | | 210 | | | | | 215 | | |

| cag | tgc | ctg | gtg | acc | gag | acc | aag | aca | agc | gtg | tcc | agg | cac | atc | tac | 724 |
|---|---|---|---|---|---|---|---|---|---|---|---|---|---|---|---|---|
| Gln | Cys | Leu | Val | Thr | Glu | Thr | Lys | Thr | Ser | Val | Ser | Arg | His | Ile | Tyr | |
| | | | | 220 | | | | | 225 | | | | | 230 | | |

| ttt | ttc | agc | gcc | aga | ggc | agg | atc | gac | ccc | ctg | gtg | tac | ctg | gac | gag | 772 |
|---|---|---|---|---|---|---|---|---|---|---|---|---|---|---|---|---|
| Phe | Phe | Ser | Ala | Arg | Gly | Arg | Ile | Asp | Pro | Leu | Val | Tyr | Leu | Asp | Glu | |
| | | | 235 | | | | | 240 | | | | | 245 | | | |

| ttc | ctg | agg | aac | agc | gag | ccc | gtg | ctg | aag | aga | gtg | aac | agg | acc | ggc | 820 |
|---|---|---|---|---|---|---|---|---|---|---|---|---|---|---|---|---|
| Phe | Leu | Arg | Asn | Ser | Glu | Pro | Val | Leu | Lys | Arg | Val | Asn | Arg | Thr | Gly | |
| | | 250 | | | | | 255 | | | | | 260 | | | | |

| | | |
|---|---|---|
| aac agc agc agc aac aag cag gag tac cag ctg ctg aag gac aac ctg<br>Asn Ser Ser Ser Asn Lys Gln Glu Tyr Gln Leu Leu Lys Asp Asn Leu<br>265                      270                      275 | | 868 |
| gtg cgc agc tac aac aag gcc ctg aag aag aac gcc ccc tac ccc atc<br>Val Arg Ser Tyr Asn Lys Ala Leu Lys Lys Asn Ala Pro Tyr Pro Ile<br>280                      285                      290                      295 | | 916 |
| ttc gct atc aag aac ggc cct aag agc cac atc ggc agg cac ctg atg<br>Phe Ala Ile Lys Asn Gly Pro Lys Ser His Ile Gly Arg His Leu Met<br>                      300                      305                      310 | | 964 |
| acc agc ttt ctg agc atg aag ggc ctg acc gag ctg aca aac gtg gtg<br>Thr Ser Phe Leu Ser Met Lys Gly Leu Thr Glu Leu Thr Asn Val Val<br>               315                      320                      325 | | 1012 |
| ggc aac tgg agc gac aag agg gcc tcc gcc gtg gcc agg acc acc tac<br>Gly Asn Trp Ser Asp Lys Arg Ala Ser Ala Val Ala Arg Thr Thr Tyr<br>          330                      335                      340 | | 1060 |
| acc cac cag atc acc gcc atc ccc gac cac tac ttc gcc ctg gtg tcc<br>Thr His Gln Ile Thr Ala Ile Pro Asp His Tyr Phe Ala Leu Val Ser<br>345                      350                      355 | | 1108 |
| agg tac tac gcc tac gac ccc atc agc aag gag atg atc gcc ctg aag<br>Arg Tyr Tyr Ala Tyr Asp Pro Ile Ser Lys Glu Met Ile Ala Leu Lys<br>360                      365                      370                      375 | | 1156 |
| gac gag acc aac ccc atc gag gag tgg cag cac atc gag cag ctg aag<br>Asp Glu Thr Asn Pro Ile Glu Glu Trp Gln His Ile Glu Gln Leu Lys<br>                      380                      385                      390 | | 1204 |
| ggc agc gcc gag ggc agc atc aga tac ccc gcc tgg aac ggc atc atc<br>Gly Ser Ala Glu Gly Ser Ile Arg Tyr Pro Ala Trp Asn Gly Ile Ile<br>          395                      400                      405 | | 1252 |
| agc cag gag gtg ctg gac tac ctg agc agc tac atc aac agg cgg atc<br>Ser Gln Glu Val Leu Asp Tyr Leu Ser Ser Tyr Ile Asn Arg Arg Ile<br>410                      415                      420 | | 1300 |
| tgatgagata tcgagctcca gcttttgttc cc | | 1332 |

<210> SEQ ID NO 2
<211> LENGTH: 423
<212> TYPE: PRT
<213> ORGANISM: Artificial
<220> FEATURE:
<223> OTHER INFORMATION: Synthetic Construct

<400> SEQUENCE: 2

Met Ser Gln Phe Asp Ile Leu Cys Lys Thr Pro Pro Lys Val Leu Val
1                  5                      10                      15

Arg Gln Phe Val Glu Arg Phe Glu Arg Pro Ser Gly Glu Lys Ile Ala
                    20                      25                      30

Ser Cys Ala Ala Glu Leu Thr Tyr Leu Cys Trp Met Ile Thr His Asn
          35                      40                      45

Gly Thr Ala Ile Lys Arg Ala Thr Phe Met Ser Tyr Asn Thr Ile Ile
    50                      55                      60

Ser Asn Ser Leu Ser Phe Asp Ile Val Asn Lys Ser Leu Gln Phe Lys
65                  70                      75                      80

Tyr Lys Thr Gln Lys Ala Thr Ile Leu Glu Ala Ser Leu Lys Lys Leu
                    85                      90                      95

Ile Pro Ala Trp Glu Phe Thr Ile Ile Pro Tyr Asn Gly Gln Lys His
                100                      105                      110

Gln Ser Asp Ile Thr Asp Ile Val Ser Ser Leu Gln Leu Gln Phe Glu
              115                      120                      125

Ser Ser Glu Glu Ala Asp Lys Gly Asn Ser His Ser Lys Lys Met Leu
          130                      135                      140

-continued

```
Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
                260                 265                 270

Gln Leu Leu Lys Asp Asn Leu Val Arg Ser Tyr Asn Lys Ala Leu Lys
            275                 280                 285

Lys Asn Ala Pro Tyr Pro Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
                340                 345                 350

His Tyr Phe Ala Leu Val Ser Arg Tyr Tyr Ala Tyr Asp Pro Ile Ser
            355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
                420
```